(12) United States Patent
Iwata et al.

(10) Patent No.: US 9,386,771 B2
(45) Date of Patent: Jul. 12, 2016

(54) PLANT DISEASE CONTROL COMPOSITION

(71) Applicant: SUMITOMO CHEMICAL COMPANY, LIMITED, Tokyo (JP)

(72) Inventors: Atsushi Iwata, Tokyo (JP); Makoto Kurahashi, Hyogo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/369,783

(22) PCT Filed: Jan. 21, 2013

(86) PCT No.: PCT/JP2013/051684
§ 371 (c)(1),
(2) Date: Jun. 30, 2014

(87) PCT Pub. No.: WO2013/111894
PCT Pub. Date: Aug. 1, 2013

(65) Prior Publication Data
US 2014/0371288 A1 Dec. 18, 2014

(30) Foreign Application Priority Data
Jan. 25, 2012 (JP) .................. 2012-012787

(51) Int. Cl.
*A01N 47/04* (2006.01)
*A01N 37/30* (2006.01)
*A01N 43/38* (2006.01)

(52) U.S. Cl.
CPC ............... *A01N 47/04* (2013.01); *A01N 37/30* (2013.01); *A01N 43/38* (2013.01)

(58) Field of Classification Search
None
See application file for complete search history.

(56) References Cited

U.S. PATENT DOCUMENTS

| | | | |
|---|---|---|---|
| 2004/0254237 A1 | 12/2004 | Nakamura et al. | |
| 2008/0200334 A1 | 8/2008 | Blasco et al. | |
| 2009/0036512 A1 | 2/2009 | Hauser-Hahn et al. | |
| 2009/0054235 A1 | 2/2009 | Mansfield et al. | |
| 2012/0010073 A1* | 1/2012 | Funke et al. | 504/100 |

FOREIGN PATENT DOCUMENTS

| | | |
|---|---|---|
| CN | 101223136 | 7/2008 |
| JP | 07-149701 | 6/1995 |
| JP | 11-255607 | 9/1999 |
| JP | 2001-139405 | 5/2001 |
| JP | 2002-532390 | 10/2002 |
| JP | 2003-176258 | 6/2003 |
| JP | 2004-189601 | 7/2004 |
| JP | 2005-232160 | 9/2005 |
| JP | 2008-521761 | 6/2008 |
| JP | 2009-501709 | 1/2009 |
| JP | 2009-519263 | 5/2009 |
| JP | 2009-132690 | 6/2009 |
| WO | 00/35277 | 6/2000 |
| WO | 2007/006734 | 1/2007 |
| WO | 2007/068367 | 6/2007 |
| WO | 2009/057668 | 5/2009 |
| WO | 2009/060734 | 5/2009 |
| WO | WO 2012082542 A2 * | 6/2012 |
| WO | WO 2012143127 A1 * | 10/2012 |

OTHER PUBLICATIONS

International Search Report dated Mar. 19, 2013, issued in International (PCT) Application No. PCT/JP2013/051684.
International Preliminary Report of Patentability dated Jul. 29, 2014, issued in International (PCT) Application No. PCT/JP2013/051684.
C.D.S. Tomlin, "The Pesticide Manual", 15th Edition (published by BCPC) ISBN 978-1-901396-18-8, pp. 154-156.
Philippine Office Action dated Jul. 2, 2015 issued in corresponding Philippine Application No. 1-2014-501676.
Chinese Office Action dated Jun. 25, 2015 issued in corresponding Chinese Patent Application No. 201380006263.7 (with English translation).
Australian Office Action dated Nov. 23, 2015, issued in corresponding Australian Application No. 2013212889.
Extended European Search Report issued May 26, 2015, in corresponding European Application No. 13740516.3.
Chilean Office Action Dated Oct. 23, 2015, issued in corresponding Chilean Patent Application No. 2014-001945 (With English Translation).
Chinese Office Action dated Jan. 14, 2016, issued in corresponding Chinese Patent Application No. 201380006263.7 (with English translation).
Office Action issued May 10, 2016 in corresponding Japanese patent application No. 2013-009040 (with English translation).

* cited by examiner

*Primary Examiner* — Nyeemah A Grazier
(74) *Attorney, Agent, or Firm* — Wenderoth, Lind & Ponack, L.L.P.

(57) ABSTRACT

To provide a plant disease control composition having excellent control effect against plant diseases.
A plant disease control composition comprising an amide compound represented by formula (I):

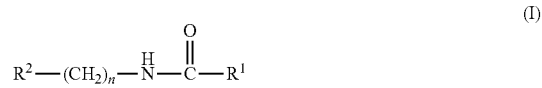

wherein each symbol is as defined in the description, and captan has excellent control effect against plant diseases.

7 Claims, No Drawings

PLANT DISEASE CONTROL COMPOSITION

TECHNICAL FIELD

The present invention relates to a plant disease control composition, and a method for controlling plant diseases.

BACKGROUND ART

A large number of compounds have hitherto been known as active ingredients of a plant disease control composition (see, for example, The Pesticide Manual—15th edition (published by BCPC) ISBN 978-1-901396-18-8).

DISCLOSURE OF INVENTION

Problems to be Solved by the Invention

An object of the present invention is to provide a plant disease control composition having excellent control effect against plant diseases.

Means for Solving the Problems

The present inventors have intensively studied so as to find a plant disease control composition having excellent control effect against plant diseases, and found that a composition comprising an amide compound represented by formula (I) shown below, and captan has excellent control effect against plant diseases.

That is, the present invention includes the following [1] to [5]:

[1] A plant disease control composition comprising:
an amide compound represented by formula (I):

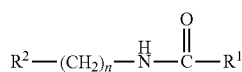

(I)

wherein
n represents any integer of from 1 to 4,
$R^1$ represents (hydroxycarbonyl)C1-C6 alkyl, (hydroxycarbonyl)C2-C6 alkenyl, (aminocarbonyl)C1-C6 alkyl, (aminocarbonyl)C2-C6 alkenyl, (C1-C6 alkoxy)carbonyl(C1-C6)alkyl, or (C1-C6 alkoxy)carbonyl(C2-C6)alkenyl, and
$R^2$ represents phenyl, 1-naphthyl, or 3-indolyl, provided that, in the substituent represented by $R^2$, any carbon atom which composes phenyl, 1-naphthyl, and 3-indolyl, and also can have a substituent, may each independently have halogen atom, hydroxyl, nitro, C1-C6 alkyl, or C1-C6 alkoxy as a substituent, and
captan;

[2] The plant disease control composition according to [1], wherein a ratio of the content of the amide compound to that of captan is from 100:1 to 1:100 in terms of a weight ratio;

[3] A method for controlling plant diseases, which comprises the step of applying of an effective amount of the plant disease control composition according to according to [1] or [2] to plants or soil in which plants are grown;

[4] A method for controlling plant diseases, which comprises the step of applying an effective amount of the plant disease control composition according to [1] or [2] to plant seeds; and

[5] The method for controlling plant diseases according to [4], wherein the plant seeds are seeds of corn, cotton, soybean, sugar beet, rapeseed, or wheat.

Effects of the Invention

According to the present invention, it is possible to control plant diseases.

MODE FOR CARRYING OUT THE INVENTION

The plant disease control composition of the present invention comprises an amide compound (hereinafter referred to as the present amide compound) represented by formula (I):

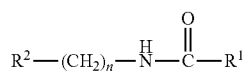

(I)

wherein
n represents any integer of from 1 to 4,
$R^1$ represents (hydroxycarbonyl)C1-C6 alkyl, (hydroxycarbonyl)C2-C6 alkenyl, (aminocarbonyl)C1-C6 alkyl, (aminocarbonyl)C2-C6 alkenyl, (C1-C6 alkoxy)carbonyl(C1-C6)alkyl, or (C1-C6 alkoxy)carbonyl(C2-C6)alkenyl, and
$R^2$ represents phenyl, 1-naphthyl, or 3-indolyl, provided that, in the substituent represented by $R^2$, any carbon atom which composes phenyl, 1-naphthyl, and 3-indolyl, and also can have a substituent, may each independently have halogen atom, hydroxyl, nitro, C1-C6 alkyl, or C1-C6 alkoxy as a substituent, and captan.

In formula (I), the (hydroxycarbonyl)C1-C6 alkyl represented by $R^1$ includes, for example, hydroxycarbonylmethyl, 2-(hydroxycarbonyl)ethyl, 3-(hydroxycarbonyl)propyl, and 4-(hydroxycarbonyl)butyl; the (hydroxycarbonyl)C2-C6 alkenyl includes, for example, 2-(hydroxycarbonyl)ethenyl, 3-(hydroxycarbonyl)-2-propenyl, and 3-(hydroxycarbonyl)-1-propenyl; the (aminocarbonyl)C1-C6 alkyl includes, for example, aminocarbonylmethyl, 2-(aminocarbonyl)ethyl, 3-(aminocarbonyl)propyl, and 4-(aminocarbonyl)butyl; the (aminocarbonyl)C2-C6 alkenyl includes, for example, 2-(aminocarbonyl)ethenyl, 3-(aminocarbonyl)-2-propenyl, and 3-(aminocarbonyl)-1-propenyl; the C1-C6 alkoxy)carbonyl(C1-C6)alkyl includes, for example, methoxycarbonylmethyl, 2-(methoxycarbonyl)ethyl, 3-(methoxycarbonyl)propyl, 4-(methoxycarbonyl)butyl, ethoxycarbonylmethyl, 2-(ethoxycarbonyl)ethyl, 3-(ethoxycarbonyl)propyl, and 4-(ethoxycarbonyl)butyl; and the (C1-C6 alkoxy)carbonyl (C2-C6)alkenyl includes, for example, 2-(methoxycarbonyl)ethenyl, 3-(methoxycarbonyl)-2-propenyl, 3-(methoxycarbonyl)-1-propenyl, 2-(ethoxycarbonyl)ethenyl, 3-(ethoxycarbonyl)-2-propenyl, and 3-(ethoxycarbonyl)-1-propenyl.

Among substituents represented by $R^2$ of formula (I), each of which may be independently included in any carbon atom which composes phenyl, 1-naphthyl, and 3-indolyl, and also can have a substituent,
the halogen atom includes, for example, fluorine atom, chlorine atom, bromine atom, and iodine atom;
the C1-C6 alkyl includes, for example, methyl, ethyl, propyl, butyl, pentyl, hexyl, 1-methylethyl, 2-methylpropyl, 3-methylbutyl, and 4-methylpentyl; and
the C1-C6 alkoxy includes, for example, methoxy, ethoxy, propoxy, butoxy, pentyloxy, hexyloxy, 1-methylethoxy, 2-methylpropoxy, 3-methylbutoxy, and 4-methylpentyloxy.

In the substituent represented by R² of formula (I), two or more carbon atoms which compose phenyl, 1-naphthyl, and 3-indolyl, and also can have a substituent, sometimes have halogen atom, hydroxyl, nitro, C1-C6 alkyl, or C1-C6 alkoxy as a substituent, simultaneously. In such case, the substituents included in the respective carbon atoms may be the same or different from each other.

The aspect of the present amide compound includes, for example, the followings:

an amide compound in which R¹ is (hydroxycarbonyl)C1-C6 alkyl or (C1-C6 alkoxycarbonyl)C1-C6 alkyl, and R² is phenyl in formula (I);

an amide compound in which n is 2, R¹ is (hydroxycarbonyl)C1-C6 alkyl or (C1-C6 alkoxycarbonyl)C1-C6 alkyl, and R² is phenyl in formula (I); and an amide compound in which R¹ is (hydroxycarbonyl)C1-C3 alkyl or (C1-C2 alkoxy)carbonyl(C1-C3)alkyl, and R² is phenyl, 1-naphthyl, 3-indolyl, or 5-methyl-3-indolyl in formula (I).

The present amide compound sometimes exists in the form of a pesticidally acceptable salt depending on the existential state.

Specific examples of the present amide compound will be shown below.

Amide compounds represented by formula (I-a):

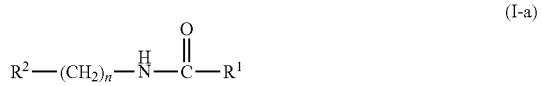

(I-a)

wherein a combination of n, R¹, and R² represents any one of combinations shown in Table 1.

TABLE 1

| Compound No. | n | R¹ | R² |
|---|---|---|---|
| 1 | 1 | hydroxycarbonylmethyl | 1-naphthyl |
| 2 | 1 | methoxycarbonylmethyl | 1-naphthyl |
| 3 | 1 | 2-(hydroxycarbonyl)ethyl | 1-naphthyl |
| 4 | 1 | 2-(hydroxycarbonyl)ethyl | phenyl |
| 5 | 1 | 3-(hydroxycarbonyl)propyl | 1-naphthyl |
| 6 | 1 | 3-(methoxycarbonyl)propyl | 1-naphthyl |
| 7 | 1 | 3-(ethoxycarbonyl)propyl | 1-naphthyl |
| 8 | 1 | 3-(propoxycarbonyl)propyl | 1-naphthyl |
| 9 | 1 | 3-(aminocarbonyl)propyl | 1-naphthyl |
| 10 | 1 | 2-(hydroxycarbonyl)ethenyl | 1-naphthyl |
| 11 | 3 | 2-(hydroxycarbonyl)ethyl | phenyl |
| 12 | 3 | 2-(methoxycarbonyl)ethyl | phenyl |
| 13 | 4 | 2-(hydroxycarbonyl)ethyl | phenyl |
| 14 | 4 | 2-(methoxycarbonyl)ethyl | phenyl |
| 15 | 3 | 3-(hydroxymethyl)propyl | phenyl |
| 16 | 3 | 3-(methoxycarbonyl)propyl | phenyl |
| 17 | 2 | 3-(hydroxycarbonyl)propyl | phenyl |
| 18 | 2 | 3-(methoxycarbonyl)propyl | phenyl |
| 19 | 2 | 3-(hydroxycarbonyl)propyl | 3-indolyl |
| 20 | 2 | 3-(methoxycarbonyl)propyl | 3-indolyl |
| 21 | 2 | 3-(ethoxycarbonyl)propyl | 3-indolyl |
| 22 | 2 | 3-(propoxycarbonyl)propyl | 3-indolyl |
| 23 | 2 | 3-(hydroxycarbonyl)propyl | 5-methyl-3-indolyl |
| 24 | 2 | 3-(hydroxycarbonyl)propyl | 1-naphthyl |
| 25 | 2 | 3-(methoxycarbonyl)propyl | 1-naphthyl |
| 26 | 2 | 3-(ethoxycarbonyl)propyl | 1-naphthyl |
| 27 | 2 | 3-(hydroxycarbonyl)butyl | phenyl |
| 28 | 2 | 3-(methoxycarbonyl)butyl | phenyl |
| 29 | 2 | 2-(methoxycarbonyl)ethyl | phenyl |
| 30 | 2 | 2-(ethoxycarbonyl)ethyl | phenyl |
| 31 | 2 | 2-(propoxycarbonyl)ethyl | phenyl |
| 32 | 2 | 2-(2-methylethoxycarbonyl)ethyl | phenyl |
| 33 | 2 | 2-(methoxycarbonyl)ethyl | 4-fluorophenyl |

TABLE 1-continued

| Compound No. | n | R¹ | R² |
|---|---|---|---|
| 34 | 2 | 2-(methoxycarbonyl)ethyl | 4-chlorophenyl |
| 35 | 2 | 2-(methoxycarbonya)ethyl | 4-bromophenyl |
| 36 | 2 | 2-(methoxycarbonyl)ethyl | 4-iodophenyl |
| 37 | 2 | 2-(methoxycarbonyl)ethyl | 2-chlorophenyl |
| 38 | 2 | 2-(methoxycarbonyl)ethyl | 3-chlorophenyl |
| 39 | 2 | 2-(methoxycarbonyl)ethyl | 3,4-dichlorophenyl |
| 40 | 2 | 2-(hydroxycarbonyl)ethyl | 4-methylphenyl |
| 41 | 2 | 2-(hydroxycarbonyl)ethyl | 4-methoxyphenyl |
| 42 | 2 | 2-(hydroxycarbonyl)ethyl | 4-fluorophenyl |
| 43 | 2 | 2-(hydroxycarbonyl)ethyl | 4-chlorophenyl |
| 44 | 2 | 2-(hydroxycarbonyl)ethyl | 4-bromophenyl |
| 45 | 2 | 2-(hydroxycarbonyl)ethyl | 4-iodophenyl |
| 46 | 2 | 2-(hydroxycarbonyl)ethyl | 4-nitrophenyl |
| 47 | 2 | 2-(hydroxycarbonyl)ethyl | 2-chlorophenyl |
| 48 | 2 | 2-(hydroxycarbonyl)ethyl | 3,4-dichlorophenyl |
| 49 | 2 | 2-(hydroxycarbonyl)ethyl | phenyl |
| 50 | 2 | 4-(methoxycarbonyl)butyl | phenyl |
| 51 | 2 | 4-(hydroxycarbonyl)butyl | phenyl |

The present amide compound is a compound disclosed, for example, in Japanese Unexamined Patent Publication (Kokai) No. 11-255607 and Japanese Unexamined Patent Publication (Kokai) No. 2001-139405, and can be synthesized, for example, by the methods disclosed in the publications.

Captan used in the present invention is a known compound and is disclosed, for example, in "The Pesticide Manual-15th edition (published by BCPC); ISBN 978-1-901396-18-8" on page 154. These compounds are obtained from commercially available formulations, or they can be produced by a known method.

In the plant disease control composition of the present invention, the weight ratio of the present amide compound to captan is not particularly limited, and the amount of captan is usually from 10 to 100,000 parts by weight, and preferably from 100 to 10,000 parts by weight, based on 1,000 parts by weight of the present amide compound.

The plant disease control composition of the present invention may be a mixture per se of the present amide compound and captan, and is usually obtained by mixing the present amide compound with captan and an inert carrier, optionally adding a surfactant and other auxiliaries for formulation, and then formulating the mixture into an oil solution, an emulsifiable concentrate, a flowable formulation, a wettable powder, a water dispersible granule, a dust, or a granule.

The thus formulated plant disease control composition can be used directly as a plant disease control agent, or used after the addition of other inert ingredients.

The total amount of the present amide compound and captan in the plant disease control composition of the present invention is usually within a range from 0.1% to 100% by weight, preferably from 0.2 to 90% by weight, and more preferably from 1 to 80% by weight.

Examples of the inert carrier used in the case of formulation include a solid carrier and a liquid carrier. Examples of the solid carrier include fine powders or granules of minerals such as kaolin clay, attapulgite clay, bentonite, montmorillonite, acidic white clay, pyrophylite, talc, diatomaceous earth, and calcite; natural organic substances such as corncob flour and walnut shell flour; synthetic organic substances such as urea; salts such as calcium carbonate and ammonium sulfate; and synthetic inorganic substances such as synthetic hydrated silicon oxide. Examples of the liquid carrier include aromatic hydrocarbons such as xylene, alkylbenzene, and methylnaphthalene; alcohols such as 2-propanol, ethylene glycol, propylene glycol, and ethylene glycol monoethyl ether; ketones such as acetone, cyclohexanone, and isophorone; vegetable oils such as soybean oil and cottonseed oil; and petroleum-based aliphatic hydrocarbons, esters, dimethyl sulfoxide, acetonitrile, and water.

Examples of the surfactant include anionic surfactants such as alkyl sulfate ester salts, alkylaryl sulfonates, dialkyl sulfosuccinates, polyoxyethylenealkylaryl ether phosphate ester salts, lignin sulfonates, and naphthalene sulfonate formaldehyde polycondensates; nonionic surfactants such as polyoxyethylene alkylaryl ethers, polyoxyethylene alkylpolyoxypropylene block copolymers, and sorbitan fatty acid esters; and cationic surfactants such as alkyltrimethylammonium salts.

Examples of the other auxiliary for formulation include water-soluble polymers such as polyvinyl alcohol and polyvinyl pyrrolidone; polysaccharides such as gum arabic, alginic acid and a salt thereof, carboxymethyl cellulose (CMC), and xanthane gum; inorganic substances such as aluminum magnesium silicate and alumina sol; preservatives; colorants; and stabilizers such as isopropyl acid phosphate (PAP).

The plant disease control composition of the present invention can control plant diseases by applying to plants or soil in which plants are grown.

Examples of plant diseases, which can be controlled by the present invention, include the followings:

Diseases of wheat: Fusarium head blight (*Fusarium graminearum, F. avenacerum, F. culmorum, Microdochium nivale*), Typhula snow blight (*Typhula* sp., *Micronectriella nivalis*), loose smut (*Ustilago tritici, U. nuda*), bunt (*Tilletia caries*), leaf blotch (*Mycosphaerella graminicola*), and glume blotch (*Leptosphaeria nodorum*);

Diseases of corn: smut (*Ustilago maydis*) and brown spot (*Cochliobolus heterostrophus*);

Diseases of citrus: melanose (*Diaporthe citri*), scab (*Elsinoe fawcetti*), and *penicillium* rot (*Penicillium digitatum, P. italicum*);

Diseases of apple: blossom blight (*Monilinia mali*), powdery mildew (*Podosphaera leucotricha*), Alternaria leaf spot (*Alternaria alternata* apple pathotype), scab (*Venturia inaequalis*), bitter rot (*Colletotrichum acutatum*), and crown rot (*Phytophtora cactorum*);

Diseases of pear: scab (*Venturia nashicola, V. pirina*), black spot (*Alternaria alternata* Japanese pear pathotype), rust (*Gymnosporangium haraeanum*), and *phytophthora* fruit rot (*Phytophtora cactorum*);

Diseases of peach: brown rot (*Monilinia fructicola*), scab (*Cladosporium carpophilum*), and *phomopsis* rot (*Phomopsis* sp.);

Diseases of grape: anthracnose (*Elsinoe ampelina*), ripe rot (*Glomerella cingulata*), black rot (*Guignardia bidwellii*), downy mildew (*Plasmopara viticola*), and gray mold (*Botrytis cinerea*);

Diseases of Japanese persimmon: anthracnose (*Gloeosporium kaki*) and leaf spot (*Cercospora kaki, Mycosphaerella nawae*);

Diseases of gourd: anthracnose (*Colletotrichum lagenarium*), Target leaf spot (*Corynespora cassiicola*), gummy stem blight (*Mycosphaerella melonis*), Fusarium wilt (*Fusarium oxysporum*), downy mildew (*Pseudoperonospora cubensis*), and Phytophthora rot (*Phytophthora* sp.);

Diseases of tomato: early blight (*Alternaria solani*), leaf mold (*Cladosporium fulvum*), and late blight (*Phytophthora infestans*);

Diseases of cruciferous vegetables: Alternaria leaf spot (*Alternaria japonica*), white spot (*Cercosporella brassicae*), and downy mildew (*Peronospora parasitica*);

Diseases of rapeseed: sclerotinia rot (*Sclerotinia sclerotiorum*) and gray leaf spot (*Alternaria brassicae*);

Diseases of soybean: purple seed stain (*Cercospora kikuchii*), sphaceloma scab (*Elsinoe glycines*), pod and stem blight (*Diaporthe phaseolorum* var. sojae), rust (*Phakopsora pachyrhizi*), and brown stem rot (*Phytophthora sojae*);

Diseases of azuki bean: gray mold (*Botrytis cinerea*) and Sclerotinia rot (*Sclerotinia sclerotiorum*);

Diseases of kidney bean: gray mold (*Botrytis cinerea*), sclerotinia seed rot (*Sclerotinia sclerotiorum*), and kidney bean anthracnose (*Colletotrichum lindemthianum*);

Diseases of peanut: leaf spot (*Cercospora personata*), brown leaf spot (*Cercospora arachidicola*), and southern blight (*Sclerotium rolfsii*);

Diseases of potato: early blight (*Alternaria solani*) and late blight (*Phytophthora infestans*);

Diseases of cotton: Fusarium wilt (*Fusarium oxysporum*); Diseases of tobacco: brown spot (*Alternaria longipes*), anthracnose (*Colletotrichum tabacum*), downy mildew (*Peronospora tabacina*), and black shank (*Phytophthora nicotianae*);

Diseases of sugar beat: Cercospora leaf spot (*Cercospora beticola*), leaf blight (*Thanatephorus cucumeris*), Root rot (*Thanatephorus cucumeris*), and *Aphanomyces* root rot (*Aphanidermatum cochlioides*);

Diseases of rose: black spot (*Diplocarpon rosae*) and powdery mildew (*Sphaerotheca pannosa*);

Diseases of *chrysanthemum* and asteraceous plants: downy mildew (*Bremia lactucae*) and leaf blight (*Septoria chrysanthemi-indici*);

Diseases of various plants: diseases caused by *Pythium* spp. (*Pythium aphanidermatum, Pythium debarianum, Pythium graminicola, Pythium irregulare, Pythium ultimum*), gray mold (*Botrytis cinerea*), Sclerotinia rot (*Sclerotinia sclerotiorum*), and Damping-off (*Rhizoctonia solani*) caused by *Rhizoctonia* spp.;

Disease of Japanise radish: *Alternaria* leaf spot (*Alternaria brassicicola*);

Diseases of turfgrass: dollar spot (*Sclerotinia homeocarpa*), brown patch, and large patch (*Rhizoctonia solani*);

Disease of banana: sigatoka (*Mycosphaerella fijiensis, Mycosphaerella musicola, Pseudocercospora musae*); and Seed diseases or diseases in the early stages of the growth of various plants caused by bacteria of *Aspergillus* genus, *Penicillium* genus, *Fusarium* genus, Tricoderma genus, *Thielaviopsis* genus, *Rhizopus* genus, *Mucor* genus, *Phoma* genus, and *Diplodia* genus.

The plant disease control composition of the present invention is applied to crop lands such as cultivated lands, paddy fields, lawns, and orchards, or non-crop lands. The plant disease control composition of the present invention can control plant diseases in crop lands in which "plants" are grown.

Examples of plants, to which the plant disease control composition of the present invention can be applied, include the followings:

Crops: corn, rice, wheat, barley, rye, oat, sorghum, cotton, soybean, adzuki bean, peanut, buckwheat, sugar beet, rapeseed, sunflower, sugar cane, and tobacco, etc.;

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, rapeseed, etc.), Compositae vegetables (burdock, garland *chrysanthemum*, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese basil, mint, basil, etc.), strawberry, sweat potato, yam, aroid, etc.;

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date palm, coconut, oil palm, etc.;

Trees other than fruit trees: tea, mulberry, flowering trees (azalea, *camellia, hydrangea*, sasanqua, Japanese star anise, cherry, tulip tree, crape myrtle, orange osmanthus, etc.), street trees (ash tree, birch, dogwood, *eucalyptus*, ginkgo, lilac, maple tree, oak, poplar, *cercis*, Chinese sweet gum, plane tree, *zelkova*, Japanese arborvitae, fir tree, Japanese hemlock, needle juniper, pine, spruce, yew, elm, horse chestnut, etc.), coral tree, podocarpus, cedar, Japanese cypress, croton, *Euonymus japonicus, Photinia glabra*, etc.;

Lawns: Zoysia (zoysiagrass, Zoysia matrella, etc.), Bermuda grasses (Cynodon dactylon, etc.), bent grasses (Agrostis alba, creeping bent grass, hiland bent, etc.), bluegrasses (meadow grass, bird grass, etc.), fescue (tall fescue, chewings fescue, creeping red fescue, etc.), ryegrasses (darnel, rye grass, etc.), orchard grass, timothy grass, etc.; and Others: flowers (rose, carnation, *chrysanthemum*, prairie gentian, *gypsophila, gerbera*, marigold, *salvia, petunia, verbena*, tulip, aster, gentian, lily, pansy, cyclamen, orchid, *convallaria*, lavender, stock, ornamental cabbage, *primula*, poinsettia, *gladiolus*, cattleya, daisy, cymbidium, *begonia*, etc.), bio-fuel plants (Jatropha, safflower, camelina, switchgrass, *Miscanthus*, reed canary grass, giant reed, kenaf, cassava, willow, etc.), ornamental plants, etc.

The above "plants" may be those having resistance, which are imparted by a genetic engineering technique or a cross-breeding method.

The plant disease control composition of the present invention can control plant diseases by applying to plants or area in which plants are grown. Examples of the plant as used herein include stems and leaves of the plant, flowers of the plant, fruits of the plant, seeds of the plant, and bulbs of the plant. The bulbs as used herein mean scaly bulbs, corms, root stalks, tubers, tuberous roots, and rhizophores.

The method for controlling plant diseases of the present invention includes application of the plant disease control composition of the present invention to plants, and specific examples thereof include application to the stems and leaves of plants, such as foliage application; application to seeds of plants; and application to area in which plants are grown such as soil application.

Specific examples of the method of application to the stems and leaves of plants, such as foliage application include a method of applying to surfaces of plants which are grown, by ground application which is conducted using a hand sprayer, a power sprayer, a boom sprayer, or a PANCRU-sprayer; or aerial application which is conducted using aerial control or an unmanned helicopter.

The treatment of seeds of plants in the present invention is, for example, a treatment of seeds or bulbs of plants with the plant disease control composition of the present invention. Specific examples thereof include spraying treatment of spraying over surfaces of seeds or bulbs, spray coating treatment of spray coating seeds or bulbs, immersion treatment, film coating treatment, and pellet coating treatment.

Specific examples of the application to area in which plants are grown, such as soil treatment or submerged application in the present invention include planting hole application, plant foot application, in-furrow application, overall application, side ditch application, nursery box application, nursery bed application, and nursery soil incorporation.

When the plant disease control composition of the present invention is applied to plants or area in which plants are grown, the application amount varies depending on the kinds of plants, the kinds or population size of plant diseases to be controlled, the form of a formulation, the timing of application, and weather conditions. The application amount is usually from 0.05 to 10,000 g, and preferably from 0.5 to 1,000 g, per 1,000 m$^2$ of an area in which plants are grown, in terms of the total amount of the present amide compound and captan.

When seeds of plants are treated with the plant disease control composition of the present invention, the amount varies depending on the kinds of plants, the kinds or population size of plant diseases to be controlled, the form of a formulation, the timing of application, and weather conditions. The amount is usually from 0.001 to 100 g, and preferably from 0.05 to 50 g, per 1 kg of seeds, in terms of the total amount of the present amide compound and captan.

The plant disease control composition of the present invention in the form of an emulsifiable concentrate, a wettable powder, and a flowable formulation is usually applied by spraying after dilution with water. In this case, the total concentration of the present amide compound and captan is usually within a range from 0.00001 to 10% by weight, and preferably from 0.0001 to 5% by weight.

A dust and a granule are usually applied as they are without dilution.

EXAMPLES

The present invention will be described in more detail by way of Formulation Examples and Test Examples, but the present invention is not limited only thereto. In the Examples, parts are by weight unless otherwise specified. In the Examples, compounds specified by the description of the "present amide compound (compound No. 4)" are the same as those specified by "compound No." corresponding to the description of Table 1.

First, Formulation Examples will be shown.

Formulation Example 1

Ten (10) parts the present amide compound (compound No. 5), 2 parts of captan, 35 parts of a mixture (in a weight ratio of 1:1) of white carbon, polyoxyethylene alkyl ether sulfate ammonium salt, and water are mixed to a total amount of 100 parts, and then the mixture is finely ground by a wet grinding method to obtain a formulation.

Formulation Example 2

The same procedure as in Formulation Example 1 is conducted, except that the present amide compound (compound No. 13) is used in place of the present amide compound (compound No. 5), to obtain a formulation.

Formulation Example 3

The same procedure as in Formulation Example 1 is conducted, except that the present amide compound (compound No. 14) is used in place of the present amide compound (compound No. 5), to obtain a formulation.

Formulation Example 4

The same procedure as in Formulation Example 1 is conducted, except that the present amide compound (compound No. 19) is used in place of the present amide compound (compound No. 5), to obtain a formulation.

Formulation Example 5

The same procedure as in Formulation Example 1 is conducted, except that the present amide compound (compound No. 29) is used in place of the present amide compound (compound No. 5), to obtain a formulation.

Formulation Example 6

The same procedure as in Formulation Example 1 is conducted, except that the present amide compound (compound No. 36) is used in place of the present amide compound (compound No. 5), to obtain a formulation.

Formulation Example 7

The same procedure as in Formulation Example 1 is conducted, except that the present amide compound (compound No. 42) is used in place of the present amide compound (compound No. 5), to obtain a formulation.

Formulation Example 8

The same procedure as in Formulation Example 1 is conducted, except that the present amide compound (compound No. 49) is used in place of the present amide compound (compound No. 5), to obtain a formulation.

Formulation Example 9

Ten (10) parts the present amide compound (compound No. 5), 4 parts of captan, 1.5 parts of sorbitan trioleate, and 28 parts of an aqueous solution containing 2 parts of polyvinyl alcohol are mixed, and then the mixture is finely ground by a wet grinding method. An aqueous solution containing 0.05 part of xanthane gum and 0.1 part of magnesium aluminum silicate is added in this mixture to a total amount of 90 parts, and 10 parts of propylene glycol is added, followed by mixing with stirring to obtain a formulation.

Formulation Example 10

The same procedure as in Formulation Example 9 is conducted, except that the present amide compound (compound No. 13) is used in place of the present amide compound (compound No. 5), to obtain a formulation.

Formulation Example 11

The same procedure as in Formulation Example 9 is conducted, except that the present amide compound (compound No. 14) is used in place of the present amide compound (compound No. 5), to obtain a formulation.

Formulation Example 12

The same procedure as in Formulation Example 9 is conducted, except that the present amide compound (compound No. 19) is used in place of the present amide compound (compound No. 5), to obtain a formulation.

Formulation Example 13

The same procedure as in Formulation Example 9 is conducted, except that the present amide compound (compound No. 29) is used in place of the present amide compound (compound No. 5), to obtain a formulation.

Formulation Example 14

The same procedure as in Formulation Example 9 is conducted, except that the present amide compound (compound No. 36) is used in place of the present amide compound (compound No. 5), to obtain a formulation.

Formulation Example 15

The same procedure as in Formulation Example 9 is conducted, except that the present amide compound (compound No. 42) is used in place of the present amide compound (compound No. 5), to obtain a formulation.

Formulation Example 16

The same procedure as in Formulation Example 9 is conducted, except that the present amide compound (compound No. 49) is used in place of the present amide compound (compound No. 5), to obtain a formulation.

Formulation Example 17

Ten (10) parts of the present amide compound (compound No. 5), 10 parts of captan, 3 parts of calcium lignin sulfonate 2 parts of sodium lauryl sulfate, and synthetic hydrated silicon oxide as balance are well ground and mixed to obtain 100 parts of a formulation.

Formulation Example 18

The same procedure as in Formulation Example 17 is conducted, except that the present amide compound (compound No. 13) is used in place of the present amide compound (compound No. 5), to obtain a formulation.

Formulation Example 19

The same procedure as in Formulation Example 17 is conducted, except that the present amide compound (compound No. 14) is used in place of the present amide compound (compound No. 5), to obtain a formulation.

Formulation Example 20

The same procedure as in Formulation Example 17 is conducted, except that the present amide compound (compound No. 19) is used in place of the present amide compound (compound No. 5), to obtain a formulation.

Formulation Example 21

The same procedure as in Formulation Example 17 is conducted, except that the present amide compound (compound No. 29) is used in place of the present amide compound (compound No. 5), to obtain a formulation.

Formulation Example 22

The same procedure as in Formulation Example 17 is conducted, except that the present amide compound (compound No. 36) is used in place of the present amide compound (compound No. 5), to obtain a formulation.

Formulation Example 23

The same procedure as in Formulation Example 17 is conducted, except that the present amide compound (compound No. 42) is used in place of the present amide compound (compound No. 5), to obtain a formulation.

Formulation Example 24

The same procedure as in Formulation Example 17 is conducted, except that the present amide compound (compound No. 49) is used in place of the present amide compound (compound No. 5), to obtain a formulation.

Treatment Example 1

The formulation prepared in Formulation Example 1 is subjected to a spray coating treatment in an amount of 500 ml per 100 kg of dried sorghum seeds using a rotary seed treatment machine (seed dresser, manufactured by Hans-Ulrich Hege GmbH) to obtain treated seeds.

The same procedure as mentioned above is conducted, except that the respective formulations prepared in Formulation Examples 2 to 16 are used in place of the formulation prepared in Formulation Example 1, to obtain the respective treated seeds.

Treatment Example 2

The formulation prepared in Formulation Example 1 is subjected to a spray coating treatment in an amount of 40 ml per 10 kg of dried corn seeds using a rotary seed treatment machine (seed dresser, manufactured by Hans-Ulrich Hege GmbH) to obtain treated seeds.

The same procedure as mentioned above is conducted, except that the respective formulations prepared in Formulation Examples 2 to 16 are used in place of the formulation prepared in Formulation Example 1, to obtain the respective treated seeds.

Treatment Example 3

The formulation prepared in Formulation Example 17 is subjected to a powder coating treatment in an amount of 50 g per 10 kg of dried corn seeds to obtain treated seeds.

The same procedure as mentioned above is conducted, except that the respective formulations prepared in Formulation Examples 18 to 24 are used in place of the formulation prepared in Formulation Example 17, to obtain the respective treated seeds.

Treatment Example 4

The formulation prepared in Formulation Example 1 is subjected to a spray coating treatment in an amount of 50 ml per 10 kg of dried soybean seeds using a rotary seed treatment machine (seed dresser, manufactured by Hans-Ulrich Hege GmbH) to obtain treated seeds.

The same procedure as mentioned above is conducted, except that the respective formulations prepared in Formulation Examples 2 to 16 are used in place of the formulation prepared in Formulation Example 1, to obtain the respective treated seeds.

The effects of the present invention will be illustrated below by way of Test Examples.

Test Example 1

Each of the present amide compounds and captan was dissolved in dimethyl sulfoxide (DMSO) so as to obtain the concentration that is 150 times the test concentration, and a DMSO solution of each of the present amide compounds and a DMSO solution of captan were respectively dispensed into each well of a titer plate (with 96 wells) in the amount of 1 μl. Then, 148 μl of a suspension of a potato dextrose liquid medium containing sporidia of smut of corn (*Ustilago maydis*) suspended in advance therein, so as to obtain the concentration of $5 \times 10^4$ sporidia/ml, was added. The plate thus obtained was used as a plate in a treated area.

In contrast, 2 μl of DMSO was dispensed into each well of a titer plate (with 96 wells), and then 148 μl of a suspension of a potato dextrose liquid medium containing sporidia of smut of corn suspended in advance therein, so as to obtain the concentration of $5 \times 10^4$ sporidia/ml, was added in the same manner as in the case of the treated area. The plate thus obtained was used as a plate in a non-treated area.

Each of the plate in a treated area and the plate in a non-treated area was cultured at 18° C. for 5 days, thereby allowing smut of corn to undergo proliferation, and then the absorbance at 550 nm of each well of the titer plate was measured. The value obtained by subtracting the absorbance of the well, into which 150 μl of only a potato dextrose liquid medium has been dispensed, from this value was regarded as the degree of growth of smut of corn.

Based on the calculated degree of growth in a treated area and the calculated degree of growth in non-treated area, bactericidal effect was calculated using Equation 1.

Bactericidal effect = $100 \times (A-B)/A$       "Equation 1"

where
A: Degree of bacterial growth in non-treated area
B: Degree of bacterial growth in treated area

TABLE 2

| Test compounds | Test concentration (ppm) | Bactericidal effect |
|---|---|---|
| Present amide compound (compound No. 5) + Captan | 50 + 10 | 100 |
| Present amide compound (compound No. 5) + Captan | 25 + 100 | 100 |
| Present amide compound (compound No. 13) + Captan | 50 + 10 | 100 |
| Present amide compound (compound No. 13) + Captan | 25 + 100 | 100 |
| Present amide compound (compound No. 14) + Captan | 50 + 10 | 100 |
| Present amide compound (compound No. 14) + Captan | 25 + 100 | 99 |
| Present amide compound (compound No. 19) + Captan | 50 + 10 | 100 |
| Present amide compound (compound No. 19) + Captan | 25 + 100 | 99 |
| Present amide compound (compound No. 29) + Captan | 50 + 10 | 100 |
| Present amide compound (compound No. 29) + Captan | 25 + 100 | 100 |
| Present amide compound (compound No. 36) + Captan | 50 + 10 | 100 |
| Present amide compound (compound No. 36) + Captan | 25 + 100 | 98 |
| Present amide compound (compound No. 49) + Captan | 50 + 10 | 100 |

TABLE 2-continued

| Test compounds | Test concentration (ppm) | Bactericidal effect |
|---|---|---|
| Present amide compound (compound No. 49) + Captan | 25 + 100 | 98 |

Test Example 2

Each of the present amide compounds and captan was dissolved in dimethyl sulfoxide (DMSO) so as to obtain the concentration that is 150 times the test concentration, and a DMSO solution of each of the present amide compounds and a DMSO solution of captan were respectively dispensed into each well of a titer plate (with 96 wells) in the amount of 1 μl. Then, 148 μl of a suspension of a potato dextrose liquid medium containing conidia of leaf blotch of wheat (*Mycosphaerella graminicola*) suspended in advance therein, so as to obtain the concentration of $1 \times 10^5$ conidia/ml, was added. The plate thus obtained was used as a plate in a treated area.

In contrast, 2 μl of DMSO was dispensed into each well of a titer plate (with 96 wells), and then 148 μl of a suspension of a potato dextrose liquid medium containing conidia of leaf blotch of wheat suspended in advance therein, so as to obtain the concentration of $5 \times 10^4$ sporidia/ml, was added in the same manner as in the case of the treated area. The plate thus obtained was used as a plate in a non-treated area.

Each of the plate in a treated area and the plate in a non-treated area was cultured at 18° C. for 5 days, thereby allowing leaf blotch of wheat to undergo proliferation, and then the absorbance at 550 nm of each well of the titer plate was measured. The value obtained by subtracting the absorbance of the well, into which 150 μl of only a potato dextrose liquid medium has been dispensed, from this value was regarded as the degree of growth of leaf blotch of wheat. Based on the calculated degree of growth in a treated area and the calculated degree of growth in non-treated area, bactericidal effect was calculated using Equation 1.

TABLE 3

| Test compounds | Test concentration (ppm) | Bactericidal effect |
|---|---|---|
| Present amide compound (compound No. 5) + Captan | 50 + 10 | 100 |
| Present amide compound (compound No. 5) + Captan | 25 + 100 | 100 |
| Present amide compound (compound No. 13) + Captan | 50 + 10 | 100 |
| Present amide compound (compound No. 13) + Captan | 25 + 100 | 100 |
| Present amide compound (compound No. 14) + Captan | 50 + 10 | 100 |
| Present amide compound (compound No. 14) + Captan | 25 + 100 | 100 |
| Present amide compound (compound No. 19) + Captan | 50 + 10 | 100 |
| Present amide compound (compound No. 19) + Captan | 25 + 100 | 100 |
| Present amide compound (compound No. 29) + Captan | 50 + 10 | 100 |
| Present amide compound (compound No. 29) + Captan | 25 + 100 | 100 |

TABLE 3-continued

| Test compounds | Test concentration (ppm) | Bactericidal effect |
|---|---|---|
| Present amide compound (compound No. 36) + Captan | 50 + 10 | 100 |
| Present amide compound (compound No. 36) + Captan | 25 + 100 | 100 |
| Present amide compound (compound No. 49) + Captan | 50 + 10 | 100 |
| Present amide compound (compound No. 49) + Captan | 25 + 100 | 98 |

Test Example 3

Each of the present amide compounds and captan was dissolved in dimethyl sulfoxide (DMSO) so as to obtain the concentration that is 150 times the test concentration, and a DMSO solution of each of the present amide compounds and a DMSO solution of captan were respectively dispensed into each well of a titer plate (with 96 wells) in the amount of 1 μl. Then, 148 μl of a suspension of a potato dextrose liquid medium containing conidia of *Fusarium* head blight of wheat (*Fusarium graminearum*) in advance therein, so as to obtain the concentration of $5 \times 10^3$ conidia/ml, was added. The plate thus obtained was used as a plate in a treated area.

In contrast, 2 μl of DMSO was dispensed into each well of a titer plate (with 96 wells), and then 148 μl of a suspension of a potato dextrose liquid medium containing conidia of *Fusarium* head blight of wheat suspended in advance therein, so as to obtain the concentration of $5 \times 10^4$ sporidia/ml, was added in the same manner as in the case of the treated area. The plate thus obtained was used as a plate in a non-treated area.

Each of the plate in a treated area and the plate in a non-treated area was cultured at 18° C. for 5 days, thereby allowing foot rot of wheat to undergo proliferation, and then the absorbance at 550 nm of each well of the titer plate was measured. The value obtained by subtracting the absorbance of the well, into which 150 μl of only a potato dextrose liquid medium has been dispensed, from this value was regarded as the degree of growth of *Fusarium* head blight of wheat. Based on the calculated degree of growth in a treated area and the calculated degree of growth in non-treated area, bactericidal effect was calculated using Equation 1.

TABLE 4

| Test compounds | Test concentration (ppm) | Bactericidal effect |
|---|---|---|
| Present amide compound (compound No. 5) + Captan | 50 + 10 | 100 |
| Present amide compound (compound No. 5) + Captan | 25 + 100 | 100 |
| Present amide compound (compound No. 13) + Captan | 50 + 10 | 100 |
| Present amide compound (compound No. 13) + Captan | 25 + 100 | 100 |
| Present amide compound (compound No. 14) + Captan | 50 + 10 | 100 |
| Present amide compound (compound No. 14) + Captan | 25 + 100 | 100 |
| Present amide compound (compound No. 19) + Captan | 50 + 10 | 100 |

TABLE 4-continued

| Test compounds | Test concentration (ppm) | Bactericidal effect |
| --- | --- | --- |
| Present amide compound (compound No. 19) + Captan | 25 + 100 | 100 |
| Present amide compound (compound No. 29) + Captan | 50 + 10 | 100 |
| Present amide compound (compound No. 29) + Captan | 25 + 100 | 100 |

Test Example 4

Each of the present amide compounds and captan was dissolved in dimethyl sulfoxide (DMSO) so as to obtain the concentration that is 150 times the test concentration, and a DMSO solution of each of the present amide compounds and a DMSO solution of captan were respectively dispensed into each well of a titer plate (with 96 wells) in the amount of 1 μl. Then, 148 μl of a suspension of a liquid complete medium containing conidia of gray mold (*Botrytis cinerea*) suspended in advance therein, so as to obtain the concentration of 1×10$^5$ conidia/ml, was added. The plate thus obtained was used as a plate in a treated area.

In contrast, 2 μl of DMSO was dispensed into each well of a titer plate (with 96 wells), and then 148 μl of a suspension of a liquid complete medium containing conidia of gray mold suspended in advance therein, so as to obtain the concentration of 1×10$^5$ sporidia/ml, was added in the same manner as in the case of the treated area. The plate thus obtained was used as a plate in a non-treated area.

Each of the plate in a treated area and the plate in a non-treated area was cultured at 18° C. for 4 days, thereby allowing gray mold to undergo proliferation, and then the absorbance at 550 nm of each well of the titer plate was measured. The value obtained by subtracting the absorbance of the well, into which 150 μl of only a liquid complete medium has been dispensed, from this value was regarded as the degree of growth of gray mold. Based on the calculated degree of growth in a treated area and the calculated degree of growth in non-treated area, bactericidal effect was calculated using Equation 1.

TABLE 5

| Test compounds | Test concentration (ppm) | Bactericidal effect |
| --- | --- | --- |
| Present amide compound (compound No. 4) + Captan | 1.3 + 0.63 | 99 |
| Present amide compound (compound No. 11) + Captan | 1.3 + 0.63 | 96 |
| Present amide compound (compound No. 13) + Captan | 1.3 + 0.63 | 97 |
| Present amide compound (compound No. 14) + Captan | 1.3 + 0.63 | 96 |
| Present amide compound (compound No. 19) + Captan | 2.5 + 0.63 | 96 |
| Present amide compound (compound No. 31) + Captan | 2.5 + 0.63 | 97 |

TABLE 5-continued

| Test compounds | Test concentration (ppm) | Bactericidal effect |
| --- | --- | --- |
| Present amide compound (compound No. 32) + Captan | 1.3 + 0.63 | 96 |
| Present amide compound (compound No. 40) + Captan | 1.3 + 0.63 | 97 |
| Present amide compound (compound No. 43) + Captan | 1.3 + 0.63 | 97 |
| Present amide compound (compound No. 50) + Captan | 1.3 + 0.63 | 96 |

The invention claimed is:

1. A plant disease control composition comprising:
an amide compound represented by formula (I):

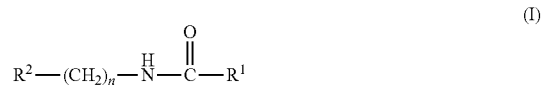

wherein
n represents any integer of from 1 to 4,
R$^1$ represents (hydroxycarbonyl)C1-C6 alkyl, (hydroxycarbonyl)C2-C6 alkenyl, (aminocarbonyl)C1-C6 alkyl, (aminocarbonyl)C2-C6 alkenyl, (C1-C6 alkoxy)carbonyl(C1- C6) alkyl, or (C1-C6 alkoxy)carbonyl(C2-C6) alkenyl, and
R$^2$ represents phenyl, 1-naphthyl, or 3-indolyl,
provided that, in the substituent represented by R$^2$, any carbon atom which composes phenyl, 1-naphthyl, and 3-indolyl, and also can have a substituent, may each independently have a halogen atom, hydroxyl, nitro, C1-C6 alkyl, or C1-C6 alkoxy as a substituent, and
captan.

2. The plant disease control composition according to claim 1, wherein a ratio of the content of the amide compound to that of captan is from 100:1 to 1:100 in terms of a weight ratio.

3. A method for controlling plant diseases, which comprises the step of applying an effective amount of the plant disease control composition according to claim 1 to plants or soil in which plants are grown.

4. A method for controlling plant diseases, which comprises the step of applying an effective amount of the plant disease control composition according to claim 1 to plant seeds.

5. The method for controlling plant diseases according to claim 4, wherein the plant seeds are seeds of corn, cotton, soybean, sugar beet, rapeseed, or wheat.

6. A method for controlling plant diseases, which comprises the step of applying an effective amount of the plant disease control composition according to claim 2 to plants or soil in which plants are grown.

7. A method for controlling plant diseases, which comprises the step of applying an effective amount of the plant disease control composition according to claim 2 to plant seeds.

* * * * *